(12) United States Patent
Russo

(10) Patent No.: US 6,221,041 B1
(45) Date of Patent: Apr. 24, 2001

(54) FLUID TRANSFER DEVICE CONNECTING A MEDICINAL VESSEL AND AN IV BAG IN CLOSED SYSTEM

(75) Inventor: Antonello Russo, Trieste (IT)

(73) Assignee: Eurospital S.p.A., Trieste (IT)

( * ) Notice: Subject to any disclaimer, the term of this patent is extended or adjusted under 35 U.S.C. 154(b) by 0 days.

(21) Appl. No.: 09/555,125

(22) PCT Filed: Nov. 19, 1998

(86) PCT No.: PCT/IT98/00326

§ 371 Date: Jun. 14, 2000

§ 102(e) Date: Jun. 14, 2000

(87) PCT Pub. No.: WO99/26580

PCT Pub. Date: Jun. 3, 1999

(30) Foreign Application Priority Data

Nov. 26, 1997 (IT) .......................................... RM970254 U

(51) Int. Cl.[7] ..................................................... A61M 5/00

(52) U.S. Cl. ................................ 604/82; 604/86; 604/905

(58) Field of Search ................................. 604/82, 83, 86, 604/88, 905

(56) References Cited

FOREIGN PATENT DOCUMENTS

| 0544654 | * | 6/1993 | (EP) . |
| 1417397 | * | 12/1975 | (GB) . |
| 9408549 | * | 4/1994 | (WO) . |
| 9629113 | * | 9/1996 | (WO) . |

* cited by examiner

Primary Examiner—John D. Yasko
(74) Attorney, Agent, or Firm—Nixon Vanderhye

(57) ABSTRACT

A fluid transfer device connecting a medicinal vessel and an intravenous (IV) bag for enabling the mixing in closed system of the two products contained therein by means of a syringe, comprising a three-way plug valve assembly (3) with a first port ending in a connector (5) for a syringe, and a second and a third port (8, 7), each one provided into a respective spike (1, 2) connected to a housing (16, 17) for a container of medicinal product. Within the first one of the said two spikes (1) a further independent channel (13) is provided for the inlet and the outlet of air, communicating with the external environment through a hydrophobic filter (14). The second one of said two spikes (2) is capable of piercing the rubber closure of the injection point of a bag of medicinal product, and the corresponding housing (17) consists of two flexible arms (18, 19) fastenable to each other at the respective ends, so as to be tightened around the tube of the said injection point.

7 Claims, 3 Drawing Sheets

FLUID TRANSFER DEVICE CONNECTING A MEDICINAL VESSEL AND AN IV BAG IN CLOSED SYSTEM

The present invention concerns a fluid transfer device connecting a medicinal vessel and an intravenous (IV) bag in dosed system. More specifically, the invention relates to a device provided with a three-way valve, allowing to transfer two pharmaceutical products, respectively from a rigid container such as a bottle or a vial and from a bag-type container, by means of a syringe. The device is used to obtain the mixture of the two products by transfer from one container to the other, without removing any one of the three elements (i.e., vessel, bag and syringe) from the assembly until the end of the operation.

As it is known, many medicinal products for intravenous administration are diluted before use in suitably proportioned amounts of injectable or perfusional solutions, in order to be injected or infused to the patient by the intravenous route, i.e. in the phleboclysis form. In some cases these medicaments are placed on the market in the liquid form, e.g. as solutions or as stable suspensions, while in other cases they are in the dry powder form. Active ingredients in the dry powder form must be reconstituted before use by the addition of a measured amount of liquid. The transfer and the dilution or the reconstitution of the said medicinal products before use are conventionally carried out by means of a syringe provided with needle.

When a medicament to be reconstituted is used, a predetermined amount of injectable diluent solution or of perfusional solution is taken by means of a syringe from the relevant container, and is introduced in the bottle or vial of medicament. The latter is normally provided with a pierceable rubber stopper. Once it has been diluted, the drug is taken up from its bottle with the syringe and is administered to the patient intravenously, or it is transferred, wholly or in part, in the container of the perfusional solution, so as to obtain the desired dosage of active ingredient to be infused.

It is evident that the operations referred to above unavoidably involve the production of splashes and aerosols that diffuse through the air from the syringe, for instance when air is expelled from the syringe during the dosing operation, or when the needle is extracted from the bottle of medicament. In the particularly important case where the medicament is an anticancer drug, the medical personnel coming into contact with the drug, or breathing it, during the preparation of the intravenous infusion set is exposed to a non negligible risk. The prolonged and repeated exposure to doses even extremely reduced of such substances may result in long term effects of the same kind as those borne by the patients. For some antineoplastic drugs, such as, e.g., cyclophosphamide, a carcinogenic activity has already been ascertained, while other drugs are still under evaluation in this respect.

Another case where the formation of drug-containing aerosols is particularly harmful is the case of antibiotics. In this case the active ingredient released in the environment may cause the development of resistance by the bacterial strains present therein. The foregoing may easily result in the development of infections difficult to overcome, specially in the hospital environment.

A further problem involved by the conventional operations of transfer and reconstitution of drugs by means of a syringe is the impossibility of maintaining a complete sterility in the manipulation. The micro-organisms present in the environment or on the operator's hands may come into contact with the needle, and from here they may be carried into the solution to be infused or injected to the patient. Since the said solution is injected directly in the patient's bloodstream, the foregoing involves a remarkable risk of infections, specially in view of the weakened conditions of the patient receiving such therapies.

In order to reduce to some extent the occurrence of the first one of the problems cited above, that is the formation of splashes and aerosols, some devices known as "vented spike" are already available on the market. Such devices are spikes provided with a hydrophobic filter that are placed between the syringe (without needle) and the container of medicinal product, serving as a port for the inlet and the outlet of air during the movements of the syringe plunger and, if desired, as a filter for the liquid transferred. The vented spike devices consist of a hollow spike suitable to perforate the stopper of a pharmaceutical container in the same way as a syringe, of an aperture for the passage of air, provided with a hydrophobic filter of a porosity suitable to prevent both the passage of aerosol toward the exterior and the passage of micro-organisms towards the interior, optionally of a filter placed on the liquid path and of a connector for a syringe.

Although they actually reduce the production of aerosols, the vented ;spike devices do not constitute systems completely isolated from the exterior, as they do not connect both vessels at the same time, and require that the device be removed from the first vessel in order to transfer the liquid to the second vessel. Therefore, the risk of contamination of the medicament still exists, and the risk that the operator comes into contact with the drug is still not totally avoided.

The PCT application publ. No. 96/29113, in the name of Medimop Medical Projects Ltd. et al., discloses a transfer device for medicinal fluids having at least three ports, one of which is connected with a syringe (also in this case, without needle). The device is provided with a plug cock, that may be rotated to establish fluid communication between two of the three ports, in turn. At least one of the three ports is provided with an adaptor for connection with the upper part of a bottle, said adaptor having a hollow spike.

In some of its embodiments, the said transfer device is designed to connect a syringe, previously filled in with diluting solution, a vial of medicament to be reconstituted and, on the third port, directly the patient to be treated. Other embodiments concern the connection of two medicinal containers (through the syringe), in order to obtain a closed system that allows the blending of two different liquid products through the syringe, without removing any one of the three elements up to the completion of the operation. Such device, according to the disclosure of the document, is designed so as to allow an antiseptic administration of the drug, as it prevents any contact of the latter and of the injectable or perfusional solution with the external environment for the whole blending and dosing operation, up to the administration to the patient.

In the embodiments providing the connection of two vessels, the device at issue is endowed with two opposedly placed housings for the head of two vials or bottles, each housing being provided with a hollow spike. Between the said two housings there is provided a valve assembly consisting of a three-way plug cock with the third port connected to a housing for the syringe tip After connecting the two vessels and the syringe to the device, the cock is positioned so as to put the syringe in communication with the bottle containing the perfusional solution or with the vial containing the injectable solution, and the solution is sucked into the syringe. Then the cock is rotated so as to connect the syringe with the bottle of medicament to be reconstituted, and the liquid is injected from the syringe in the bottle. Once diluted, the medicament is sucked from its bottle and, in the case of preparation of products to be administered by infusion, the cock is rotated so as to connect again the syringe with the bottle of perfusional solution and the diluted medicament is transferred from the syringe to the bottle of solution, to give the product ready for infusion.

The last one of the 29 figures accompanying the above PCT application shows an embodiment which takes into account (at least in part) that this series of operations, carried out in a closed system, requires the presence of some apertures for the passage of air. According to the disclosure, one of the two spikes is provided with two internal channels, one for the liquid and the other for the air passage, the latter terminating in an external hydrophobic filter.

None of the solutions taught by the PCT application publ. No. WO 96/29113, however, is concerned with the case where one of the two containers to be connected is not a bottle or a vial, rather it is a flexible bag of the kind currently employed, with increasing diffusion, for perfusional solutions. In spite of the fact that this type of containers is referred to in the introduction of the application as being one of the three possible kinds of medicinal containers (along with the bottles and the ampoules), and is subsequently mentioned, generically, in the description, all of the containers shown in detail in the disclosure are rigid cylindrical vessels with pierceable rubber stopper. No specific embodiment is disclosed having a connection system suitable for use, in particular, with intravenous bags.

As it is known, the bags of liquid products for pharmaceutical use known as intravenous (IV) bags are generally rectangular containers made of flexible plastic material, closed along two or more sides by heat sealing. One or, more often, two tubular elements for accessing the contents of the bag are inserted along one edge of the bag. One of the two tubes is intended to be connected, in use, to the drip chamber of the infusion tubing, to intravenously administer to the patient the fluid contained in the bag. The other tube projecting from the bag edge, currently referred to as the injection point, is used to inject in the IV bag additional agents, such as suitably dosed drugs to be diluted into the perfusional solution contained in the bag. The tube of the injection point is normally sealed at one end by a fixed cylindrical plug made of para rubber. The latter allows to introduce a syringe needle for the injection of a drug in the IV bag and to withdraw the needle thereafter without leaving a hole in the plug. The injection point tube is often—but not always—provided with a terminal section of greater diameter at the point where the rubber plug is inserted. The size of the injection point of the IV bags currently in use is not standardised and may range, e.g., from 8 mm to 12.5 mm in diameter (at the point where the para rubber is inserted) and from less than 2 cm to more than 8 cm in length.

The design of a device for connecting two medicinal containers according to the general teachings of the PCT application publ. No. WO 96/29113 wherein one of the two containers, instead of being a conventional bottle or vial, is a bag of the type described above appears to involve some practical problems that have not been considered in the said disclosure. Such problems are mainly due to the need of providing a functional connection and a tight fastening between the transfer device and the bag, specifically between the device and the tube of the injection point. Such requirement is even more critical in view of the fact that in using the concerned device to transfer the products from one container to the other through the syringe the assembly of containers and syringe is repeatedly turned upside down. In such operations an IV bag containing a liquid product is clearly more difficult to handle than a rigid bottle.

In order to overcome the foregoing problems, the present invention provides a device wherein one of the two opposedly placed housings for the head of vials or bottles disclosed in the above PCT application is replaced by a housing with fastening means suitable to enclose the injection point tube of a bag of pharmaceutical product and to be firmly tightened around the said tube, thus preventing the bag from coming away from the assembly during the handling of the device. The hollow spike originally provided in the concerned housing is replaced by a steel needle of the kind used for syringes, or else by a spike made of plastics but capable of piercing the para rubber of the injection point of the bag.

Therefore, the present invention specifically provides a fluid transfer device connecting a medicinal vessel and an intravenous (IV) bag for enabling the mixing in dosed system of the two products contained therein, comprising a three-way plug valve assembly with a first port, provided along the rotation axis of said valve, ending in a connector for a syringe, and a second and a third port, opposite to each other and both orthogonal to said first port, each one provided into a respective spike connected to a housing for a container of medicinal product, the said valve being so shaped as to alternatively connect said first port with said second port or with said third port, wherein within the first one of the said two spikes a further independent channel is provided for the inlet and the outlet of air, communicating with the external environment through a hydrophobic filter included in the device, characterised in that the second one of the said two spikes is capable of piercing the rubber closure of the injection point of a bag of medicinal product, and in that the housing provided on said second spike consists of two flexible arms attached to the device close to the point where the said second spike is connected to the device, said arms extending substantially parallel to said second spike and being fastenable to each other at the respective ends, so as to be tightened around the tube of the said injection point.

Further structural and functional features of the device according to the invention are specified in the dependent claims. The said features, as well as the advantages of the invention, will be clearer with reference to a specific embodiment thereof, which is shown by way of example in the accompanying drawings, wherein:

Figure 1:
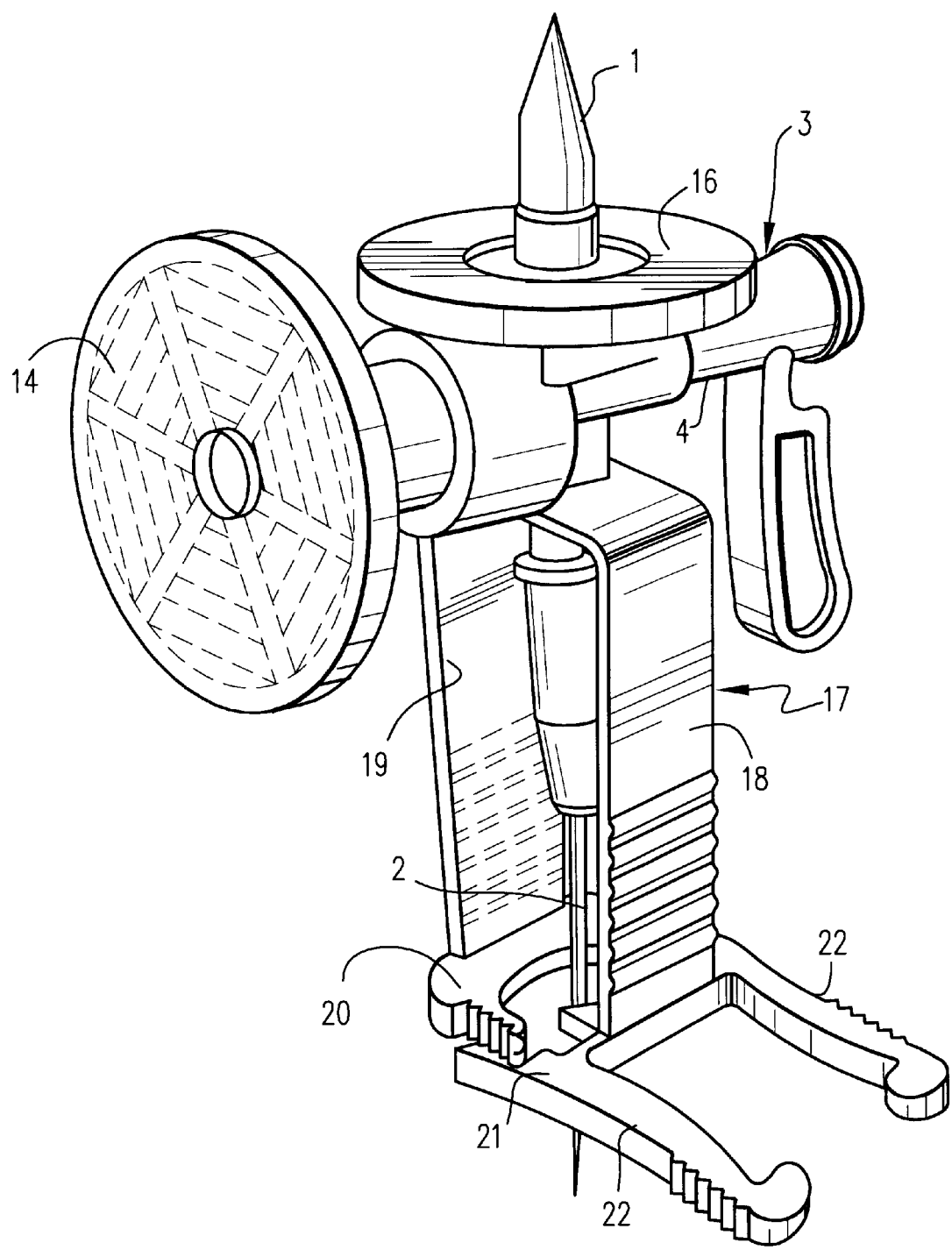
FIG. 1 is a perspective view of a fluid transfer device according to the invention.
Figure 2:
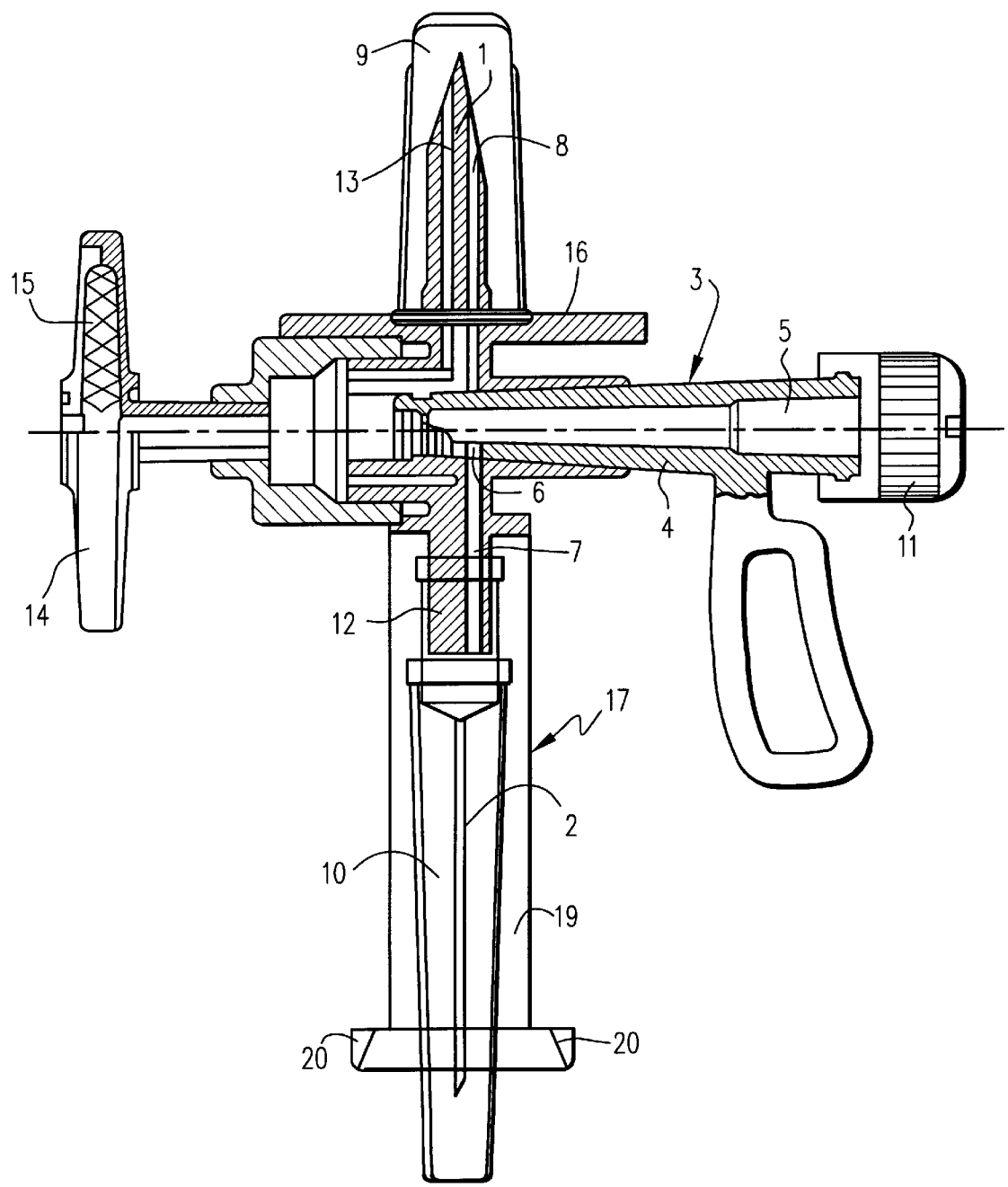
FIG. 2 is a vertical cross-sectional view of the device of FIG. 1, with some elements not sectioned.

As it is shown in FIGS. 1 and 2, the device according to the invention comprises a spike (1) capable of piercing the rubber stopper of a bottle or vial of medicament, e.g. a powder medicament to be reconstituted or a medicament in a concentrated liquid form, a second spike (2) consisting, in the embodiment shown, of a steel needle for syringes, capable of piercing the para rubber latex plug dosing a bag containing a perfusional solution and a three-way valve assembly (3). The plug (4) of the valve assembly (3) is provided with a coaxial port with a luer lock connector (5) for a needle-less syringe.

In FIGS. 1 and 2 the valve (3) is represented in the position that puts in communication—through the hole (6), the channel (7) for the liquid flow provided within the main structural body of the device, and the needle (2)—the syringe connected in (5) with a bag of perfusional or intravenous solution. By rotating the valve (3) by 180°, the hole (6) becomes aligned with the channel (8) for the liquid flow provided in the spike (1) connected to the medicament vial, thus putting the latter in communication with the syringe.

In FIG. 2 only, the spike (1) and the needle (2) are represented covered by the corresponding protection caps (9) and (10) (not sectioned), with which they are marketed. Also, the connector (5) for the syringe is (schematically) shown closed by a screw cap (11). Preferably, the device is entirely made of plastic material, except the needle; by way of example, the main body of the device can be made of polycarbonate and the valve plug (4) can be made of polypropylene. It is clear that, in the event that it is possible to produce a plastic spike capable of piercing the closure of the injection point of the bags of liquid products for intravenous infusion, the needle (2) of the device can be replaced by a spike integral with the device, thereby resulting in a device with the hollow tubular element (12) extending into a piercing tip.

The steel needle (2) of the device shown in the figures may be assembled to the plastic body of the device by means of a suitable adhesive provided on the tubular element (12), or by means of a luer lock connector of the kind normally used in syringes, or by any other type of threaded coupling between the two elements. Further, the fixed connection between the needle and the tubular element (12) of the device may be obtained through resilient fastening means, such as clamping means or clips provided on the edge of the tubular element (12).

Within the spike (1) there is provided a second channel (13) for the passage of air, so as to allow venting of the vial connected thereto during the transfer and mixing operations. The channel (13) is completely separate from the three-way valve assembly (3), and communicates with a hydrophobic filter (14). The filter (14) is provided with an internal membrane (15) (visible in the sectioned part) having a porosity of 0.22 $\mu$m, suitable to prevent both the escape of aerosol toward the exterior and the entrance of any micro organisms, which might penetrate in the system with the air sucked in from the atmosphere, thus polluting the product. The filter (14) can be made, for instance, of PVC, with a commercially available porous membrane made of a modified acrylic copolymer cast on a non-woven nylon support, post-treated for hydrophobicity through UV B beam polymerisation.

Since the second container attached to the device is a flexible bag, the problem of providing a port for the passage of air also in the connection with this container does not subsist. Actually, the IV bag adapts itself to any increase or decrease of the internal pressure by modifying its volume.

Figures 3, 4:
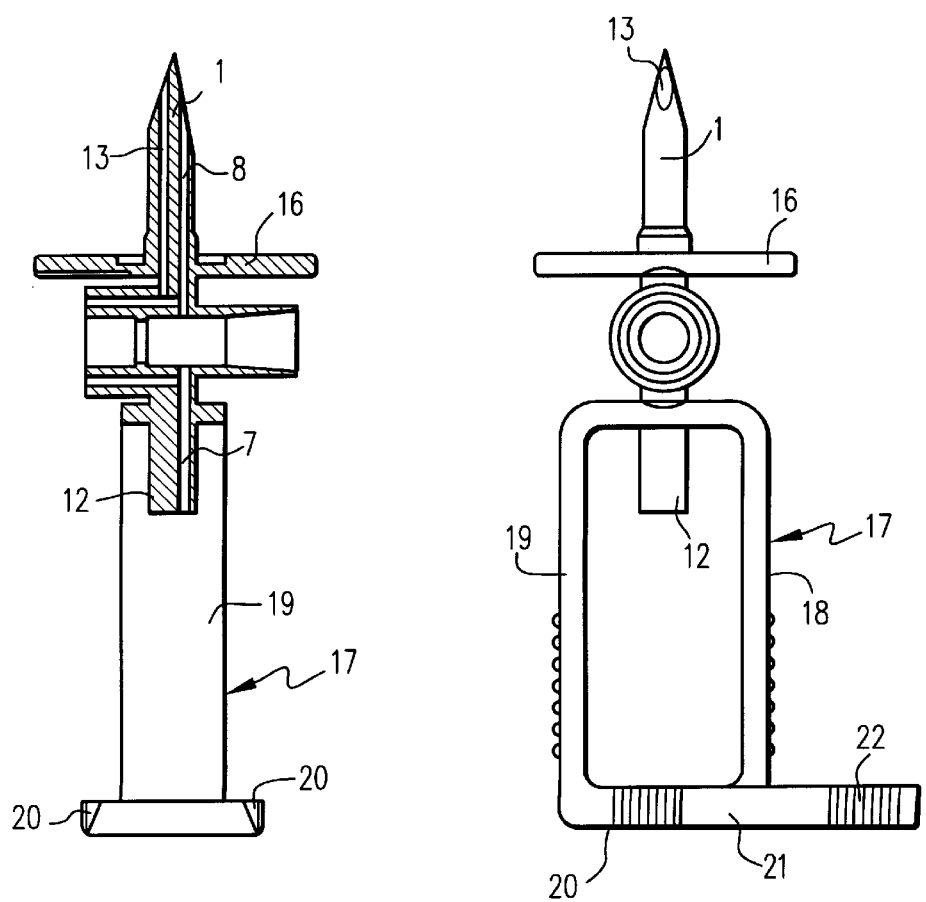
FIG. 3 is a vertical cross-sectional view of the only structural frame element of the device of FIG. 1.
FIG. 4 is a side elevation view of the same structural element of FIG. 3.

As it is shown in FIGS. 1 and 2, and in greater detail in FIGS. 3 and 4, the spike (1) for the bottle or vial of medicament is provided with a housing (16) for the latter, that consists of a circular plate on which the neck of the bottle abuts when the latter is inserted on the spike (1). The needle (2) intended to perforate the rubber plug of the IV bag is in turn provided, at the base of the tubular element (12) on which it is mounted, with a housing (17) for the injection point of the bag. The housing (17) consists of two flexible arms (18, 19) connected through an angular section to the main body of the device, which arms may be fastened to each other at their distal ends by means of two couples of locking arms (20, 21) oppositely placed. The locking arms (20, 21) are connected at an angle to the distal ends of the two arms (18, 19). The distance between the two flexible arms (18, 19) is sufficient to for them to enclose the terminal section of the injection point tube of all the IV bags currently on the market, and the flexibility of the arms allows the passage of said terminal section between the two couples of locking arms (20, 21).

Figure 5:
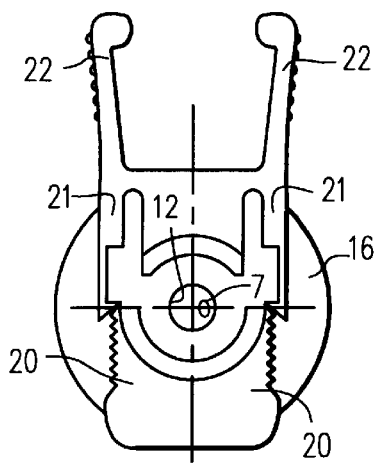
FIG. 5 is a plan view from the bottom view of the same structural element of FIG. 3.

Preferably, the two couples of locking arms (20, 21) have the shape shown in detail in FIG. 5, i.e. each of them includes a coupling with a notched profile—on the arm (20)—and a co-operating tooth—on the arm (21). On each one of the locking arms (21) bearing the tooth there is provided, at the end opposite to the said tooth, a lever projection (22) for use in disengaging the said tooth from the corresponding notched profile.

By means of the system with toothed profile and co-operating catch, and due to the flexibility of the arms (18, 19) it is possible to firmly tighten the housing (17) around the injection point tube of any bag, in spite of the fact that the said tubes have variable diameter. As it is more clearly shown in FIG. 5, to improve the grip on the tube the flexible arms (18, 19) bearing the two couples of locking arms (20, 21) both comprise, on the side facing the needle (2), a margin shaped as a circumference section, to fit the outer surface of the tube of said injection point.

The procedure of use of the device according to the invention is as follows. First, the vial containing the medicament is inserted on the spike (1), the IV bag is inserted through its injection point on the needle (2) (firmly tightening the toothed locking arms described above) and the syringe is introduced in the luer lock connector (5), with the valve (3) opening (and, correspondingly, the valve knob) turned towards the IV bag and the latter in the upward position. Then, the desired amount of liquid is sucked by means of the syringe from the bag of solution; further, the valve (3) is rotated towards the vial of medicament (which is placed in the lower position) and the solution is injected in the vial. Subsequently, the whole assembly is turned upside-down and the diluted drug is drawn in the syringe. At this stage the syringe can be disconnected to provide it with a needle and inject the diluted/reconstituted drug to the patient In the alternative, after rotating the valve (3) knob again towards the bag of solution, the diluted/reconstituted drug is introduced in the bag for the administration by infusion. The above overturning operations have the object of making the liquid always flow downwards in every transfer step.

Since the diluted medicament is sucked in the syringe with the vial placed upside-down, the corresponding spike (1) is provided, on the inlet hole of the channel (8) for the liquid passage, with a particularly sharp cut, as it is more clearly shown in FIG. 2. This arrangement makes it possible to suck completely the liquid contained in the vial without any risk of disconnecting the spike (1) from the device, as it may happen when the vial is lifted too much from its seat in order to drive the remaining liquid into the channel (8).

The present invention has been disclosed with particular reference to some specific embodiments thereof, but it should be understood that modifications and changes may be made by the persons skilled in the art without departing from the scope of the invention as defined in the appended claims.

What is claimed is:

1. A fluid transfer device connecting a medicinal vessel and an intravenous (IV) bag for enabling the mixing in closed system of the two products contained therein, comprising a three-way plug valve assembly (3) with a first port, provided along the rotation axis of said valve (3), ending in a connector (5) for a syringe, and a second and a third port (8, 7) opposite to each other and both orthogonal to said first port, each one provided into a respective spike (1, 2) connected to a housing (16, 17) for a container of medicinal product, the said valve (3) being so shaped as to alternatively connect said first port with said second port (8) or with said third port (7), wherein within the first one of the said two spikes (1) a further independent channel (13) is provided for the inlet and the outlet of air, communicating with the external environment through a hydrophobic filter (14) included in the device, characterised in that the second one of said two spikes (2) is capable of piercing the rubber closure of the injection point of a bag of medicinal product, and in that the housing (17) provided on said second spike (2) consists of two flexible arms (18, 19) attached to the device close to the point where the said second spike (2) is connected to the device, said arms (18, 19) extending substantially parallel to said second spike (2) and being fastenable to each other at the respective ends, so as to be tightened around the tube of the said injection point.

2. Device according to claim 1, wherein the said second spike is a steel needle (2) of the kind used in syringes, connected to a hollow tubular element (12) of the device, providing the corresponding port (7).

3. Device according to claim 1, wherein the said second spike is a hollow spike made of plastic material, constituting the extension of a hollow tubular element (12) of the device, providing the corresponding port (7).

4. Device according to claim 1, wherein the said two flexible arms (18, 19) are connected to the device through an angular section close to the base of said second spike (2), and are fastenable to each other, at their distal ends, by means of two couples of locking arms (20, 21) opposedly placed, connected at an angle to the said distal ends.

5. Device according to claim 4, herein each one of the said two couples of locking arms (20, 21) includes a coupling with a notched profile and a co-operating tooth.

6. Device according to claim 5, wherein each one of the said two locking arms (21) bearing the said tooth is provided, at the end opposite to said tooth, with a lever projection (22) for use in disengaging the said tooth from the corresponding notched profile.

7. Device according to claim 1, wherein the ends of said two flexible arms (18, 19) bearing the said two couples of locking arms (20, 21) both comprise, on the side facing said second spike (2), a margin shaped as a circumference section fitting the outer surface of the tube of said injection point.

* * * * *